United States Patent [19]
Lawrence et al.

[11] Patent Number: 5,922,915
[45] Date of Patent: Jul. 13, 1999

[54] PROCESS FOR REMOVING N-NITROSO COMPOUNDS FROM ORGANO-AMINE COMPOSITIONS INCLUDING DINITROANILINE HERBICIDES

[75] Inventors: Lowell J. Lawrence; Stefan Kwiatkowski, both of Lexington, Ky.

[73] Assignee: SRM Chemical, Ltd., Co., League City, Tex.

[21] Appl. No.: 09/076,015

[22] Filed: May 11, 1998

Related U.S. Application Data

[51] Int. Cl.$^6$ .......................... C07C 209/84; A01N 33/06
[52] U.S. Cl. ............................................ 564/437; 504/347
[58] Field of Search .................... 564/438, 437; 504/347

[56] References Cited

U.S. PATENT DOCUMENTS

| | | | |
|---|---|---|---|
| 3,731,901 | 5/1973 | Holdredge, Jr. | 249/180 |
| 4,023,691 | 5/1977 | Perel | 214/152 |
| 4,127,610 | 11/1978 | Eizember | 260/582 |
| 4,134,917 | 1/1979 | Ross et al. | 260/577 |
| 4,136,117 | 1/1979 | Diehl et al. | 260/577 |
| 4,185,035 | 1/1980 | Eizember et al. | 260/577 |
| 4,226,789 | 10/1980 | Eizember et al. | 260/397.7 |
| 4,338,473 | 7/1982 | Habig et al. | 568/933 |
| 4,440,962 | 4/1984 | Pallucca | 568/933 |
| 4,501,608 | 2/1985 | Cannon | 71/121 |
| 4,537,992 | 8/1985 | Pikarski et al. | 564/437 |
| 4,621,157 | 11/1986 | McDaniel | 564/411 |
| 4,675,445 | 6/1987 | Davis et al. | 564/437 |
| 4,874,895 | 10/1989 | Graziello | 564/437 |
| 4,876,388 | 10/1989 | Ravetta | 564/437 |
| 4,970,343 | 11/1990 | Pikarski et al. | 564/437 |
| 5,196,585 | 3/1993 | Wirth | 564/437 |
| 5,317,004 | 5/1994 | Misselbrook et al. | 504/116 |
| 5,391,585 | 2/1995 | Grohman | 521/139 |
| 5,405,999 | 4/1995 | Donadello | 564/437 |
| 5,444,098 | 8/1995 | Wallaeys et al. | 521/95 |
| 5,510,534 | 4/1996 | Breglia De Belcoure et al. | 564/437 |

OTHER PUBLICATIONS

M. Tanno, et al., *Thermolysis of N–Aryl–N–nitrosourceas to Afford Aryl Isocyanates and Nitrosamines via O–Nitroso–i-sourea Intermediates*, Chem. Pharm. Bull 38(10) 2644–2649(1990), vol. 38, No. 10.

D. Fine, et al., *Trace Analysis of Polar and Apolar N–Nitroso Compounds by Combined High–Performance Liquid Chromatography and Thermal Energy Analysis*, Proc. 2nd int. Symp. Nitrite Meat Prod., (191–198), Zeist, 1976. Pudoc, Wageningen.

D. Fine, et al., *Principle of Operation of the Thermal Energy Analyzer for the Trace Analysis of Volatile and Non–Volatile N–Nitroso Compounds*, Journal of Chromatography, 107 (1975) 351–357.

I. Krull, et al., *Thermal Energy Analysis for N–Nitroso Compounds*, American Laboratory (May 1979) 84–91.

*Primary Examiner*—Brian M. Burn
*Attorney, Agent, or Firm*—Arnold White & Durkee

[57] ABSTRACT

A simple and inexpensive process is described for reducing the concentration of N-nitroso-containing compounds. The process is applicable for compositions comprising N-nitroso-containing compounds and other desired compounds wherein the N-nitroso-containing compounds thermally decompose at a temperature below the decomposition temperature of the desired compounds. For compositions comprising N-nitroso-pendimethalin in Pendimethalin, the process requires heating the mixture to a temperature greater than about 120° C., and holding the Pendimethalin at that temperature for a time effective to decompose the N-nitroso-pendimethalin present in the mixture. Volatile decomposition products are advantageously removed from the composition.

24 Claims, No Drawings

PROCESS FOR REMOVING N-NITROSO COMPOUNDS FROM ORGANO-AMINE COMPOSITIONS INCLUDING DINITROANILINE HERBICIDES

FIELD OF THE INVENTION

The present invention concerns a method of quantitatively removing N-nitrosamine impurities from dinitroaniline herbicides. The present invention particularly concerns a simple, quick, and inexpensive method of eliminating both large and small quantities of N-nitroso-pendimethalin impurities from Pendimethalin by thermolysis.

BACKGROUND OF THE INVENTION

The process of manufacturing dinitroanilines produces by-products of N-nitroso compounds. The quantity of N-nitroso compounds created varies with the process used as well as the herbicide produced. For instance, Trifluralin production usually results in less than 1 weight percent of N-nitroso compounds. Conventional manufacture of Pendimethalin, on the other hand, creates between 10% and 30% by weight of N-nitroso compounds, particularly N-nitroso-pendimethalin. This nitrosamine contaminant must be reduced to very low levels, i.e., less than 1 part per million by weight (ppm) before the product can be marketed.

N-nitroso compounds, particularly alkyl nitrosamines, have been identified as carcinogens for a wide range of mammalian species. Several classes of herbicides are known to contain nitrosamine impurities. For example, substituted dinitroaniline derivatives and dimethylamine salts of phenoxyalkanoic acid are major herbicides affected by this problem. Because of the carcinogenic problem, the Environmental Protection Agency in the U.S.A. has limited the allowable concentration to be 1 ppm for N-nitroso-pendimethalin and even lower for nitrosamines in other pesticides. This, of course, has put a great burden upon producers to find ways of avoiding or eliminating such trace impurities in their products.

For a number of years now, pesticide manufacturers have been trying to reduce as much as possible the nitrosamine impurities in their products. Many processes have been developed for the herbicide Trifluralin. For Trifluralin, the parent dinitroaniline is tertiary at the amino substituent, thereby retarding the formation of N-nitroso-trifluralin during production. This resulted in far less N-nitroso compounds being formed than are formed for other related herbicides where the amino substituent is primary or secondary. Crude Trifluralin contains from between 15 to 300 ppm nitrosamine. The nitrosamine impurity in this case is primarily that of the free amine used in the amination process, i.e., N-nitroso-di-propylamine. This compound has a considerably lower molecular weight than the herbicide, allowing removal by simple steam distillation.

The N-nitroso derivative of the herbicide itself is, however, formed during the manufacture of other dinitroaniline compounds. In particular, the manufacture of Pendimethalin generally results in crude product with a N-nitroso-pendimethalin content in excess of 10% by weight. This material must be removed to a level below 1 ppm.

In the industry there currently exist three general approaches for reducing nitrosamine content. One method is to eliminate or deactivate the nitrosating agent before it can react with any amine. Another method is to convert nitrosamines to harmless products. The third method is to physically separate and destroy nitrosamines.

The first approach was taken by U.S. Pat. No. 4,120,905, which discloses the removal of nitrosating agents from 4-chloro-3,5-dinitro benzo-trifluoride in the presence of a gas and a base. Similarly, German Offenlegungsschrift No. 2,926,946 discloses purification of the dinitro benzene intermediate from nitrosating agents by crystallization. U.S. Pat. No. 4,331,468 describes a method of prevention of nitrosamine formation by the addition of monoalkanolamine retarding agent. U.S. Pat. No. 5,196,585 describes a process of reducing chloroaromatic and other impurities and stabilizing the compound against nitrosamine formation. The process utilizes an aqueous solution of sulfite. Similarly, U.S. Pat. No. 4,440,962 describes a method of removing nitrosating agents from a precursor to Trifluralin with an aqueous solution of a bisulfite. U.S. Pat. No. 4,501,608 describes a method of stabilizing dinitroanilines against nitrosamine formation by incorporating an addition compound of bisulfite with an aldehyde or ketone.

Unfortunately, these processes can not retard the formation of N-nitroso-pendimethalin in the range of ten or more percent by weight during the manufacture of Pendimethalin.

The second method for overcoming the nitrosamine problem is to decompose the already formed nitrosamines into harmless products. There are many processes in the literature to achieve this goal. U.S. Pat. No. 4,226,789 describes a method of removing nitrosamines from a herbicide by contacting the herbicide with either hydrochloric acid or gaseous hydrogen chloride. This process requires substantial quantities of HCl with concomitant additional work up of neutralization, washing and drying. In addition, it has been found that unless long reaction times and large excesses of HCl are used to remove NOCl, a byproduct, then remaining NOCl gas will immediately react with the herbicide to re-create an N-nitroso compound. In the case of Pendimethalin, the lowest practicable limit that can be reached with this method is in the range of 100 ppm N-nitroso-pendimethalin. Similarly, U.S. Pat. No. 4,185,035 converts nitrosamines utilizing compounds such a $PCl_3$ or $PCl_5$.

U.S. Pat. No. 5,405,999 describes a method of removing nitrosamines from a herbicide by contacting the herbicide with an aqueous solution of hydrogen bromide, sulfamic acid, and some form of sulfite. U.S. Pat. No. 4,874,895 also describes a method of removing nitrosamines with an aqueous solution of hydrobromic acid, sulfamic acid, and a bisulfite. The sulfamic acid serves as a scavenger for NOCl. U.S. Pat. No. 5,510,534 describes a method of removing nitrosamines from a herbicide by contacting the herbicide with an aqueous solution containing an oxidant such as alkaline persulfate.

U.S. Pat. No. 4,675,445 describes a method of removing nitrosamines by contacting the composition with an alkyl acyl halide. Similarly, U.S. Pat. No. 4,537,992 describes a method to remove nitrosamines using an acyl halide in combination with an amino-benzoate ester. U.S. Pat. No. 4,970,343 describes a process of removing nitrosamines with hydrobromo salts of an amino benzoate ester.

U.S. Pat. No. 4,127,610 describes a method of removing nitrosamines by treating the herbicide in a liquid phase with a bromine or chlorine molecule. The upper temperature limit is generally 140° C. and preferably 120° C. However, the use of 10 percent bromine was also reported to cause side reactions such as polymerization. In addition, extended exposure of the dinitroanilines with the denitrosation products under the reaction conditions was reported to result in the formation of further nitrosamines. U.S. Pat. No. 4,134, 917 describes a process to remove nitrosamines by reacting them with ketones or aldehydes in the presence of a strong acid.

The above methods use expensive chemicals and/or mineral acids. They require extended reaction times, and generate large quantities of waste products. However, the biggest problem with the majority of these methods is that the reactions are reversible, and unless all of the undesirable products of the denitrosation product are purged from the system, the reverse reaction readily occurs. It is very difficult to get the level of N-nitroso compounds below about 10 ppm using these methods.

The third method of removing nitrosamines is to physically separate them from the remaining herbicide. Several patents relate to the well-known azeotropic distillation of N-nitroso compounds with steam. This method is useful in removing N-nitroso compounds that have a lower molecular weight than the herbicide, and is therefor particularly useful for Trifluralin. U.S. Pat. No. 4,876,388 describes a method of removing nitrosamines from a herbicide by contacting the herbicide with approximately 1 to 4 times the weight of the herbicide with saturated steam at about 105° C. to 110° C. U.S. Pat. No. 4,338,473 describes a method of removing nitrosating agents from a 4-chloro-3,5-dinitrobenzotrifluoride by treating this compound with water at elevated temperatures, with at least partial removal of the water. A portion of the water is distilled off, preferably at a weak vacuum. U.S. Pat. No. 5,317,004 describes a process to manufacture microencapsulated agriculturally active compounds. The process comprises heating a low-melting material to melting, then combining this with an aqueous solution containing filming agents, homogenizing the two solutions to obtain an emulsion, and then spray drying the emulsion. The inventors discovered that during the microencapsulation step the quantity of nitrosamines in Trifluralin was reduced. For Trifluralin, however, the principal nitrosamine is N-nitroso-di-propylamine (molecular weight 130, versus 335 for Trifluralin). U.S. Pat. No. 5,728,881 describes the removal of N-nitroso-di-propylamine from crude Trifluralin by the distillation of volatile components (including water) from the final reaction mixture.

These methods result in large waste streams, and the N-nitroso compounds must still be destroyed. The processing takes as long as several hours. Furthermore, these methods are not useful when the N-nitroso compounds have a molecular weight that is equal to or greater than that of the herbicide. The azeotropic distillation with steam is not effective, therefore, in separating N-nitroso-pendimethalin (molecular weight 310) from Pendimethalin (molecular weight 218). These processes result in a considerable amount of excess material, including nitric oxide scavengers or other treatment chemicals.

What is needed is a method to quickly, economically, and quantitatively eliminate N-nitroso compounds from dinitroaniline herbicides, without adding substantial quantities, i.e., less than 2%, of other inerts to the product. In particular, what is needed is a method of reducing N-nitroso compounds to below 1 ppm in dinitroaniline herbicides, without adding substantial quantities of other inerts to the product. More particularly, what is needed is a method of reducing N-nitroso compounds to below 1 ppm in Pendimethalin, without adding substantial quantities of other inerts to the product.

SUMMARY OF THE INVENTION

We have found an inexpensive process for reducing the concentration of N-nitroso compounds. The process is applicable for mixtures of N-nitroso compounds and other desired compounds, i.e., the desired organo-amines, wherein the N-nitroso compounds thermally decompose at a temperature near or below the decomposition temperature of the desired compounds. In particular, we have found an inexpensive process for reducing the concentration of N-nitroso compounds in certain herbicides, particularly Pendimethalin.

The process involves heating a mixture of N-nitroso compounds and other compounds comprising the desired amine and optionally small quantities of a nitric oxide scavenger, to a temperature at or above the temperature where the N—NO bond in said N-nitroso compound is broken, but at a temperature near or preferably below that temperature at which the desired organo-amine decomposes.

In the particular case of Pendimethalin, the process requires heating the mixture to a temperature greater than about 120° C., and holding the Pendimethalin at that temperature for a time effective to decompose N-nitroso-pendimethalin present in the mixture to a desired final concentration. The effective time is a function of the original concentration of N-nitroso compounds, the methods of removing nitric oxide (NO) from the mixture, the desired maximum concentration of N-nitroso compounds in the product, and the temperature profile. At temperatures between about 120° C. and about 140° C. the effective time may be on the order of days. At about 160° C. the effective time may be a day or less. At about 170° C. the effective time may be 8 hours or less, while at about 180° C., the effective time may be 60 minutes or less. At very high temperatures, such as above about 210° C., the required reaction time may be a few minutes or less.

Volatile decomposition products are advantageously removed from the molten Pendimethalin, for example by applying a vacuum, or by purging with an inert gas such as nitrogen, by using nitric oxide scavengers, or by using combinations of these or other methods. It is possible to recover Pendimethalin so treated that contains less than 1 ppm N-nitroso-pendimethalin.

DETAILED DESCRIPTION OF THE INVENTION

The present invention describes an inexpensive, simple process for reducing the concentration of N-nitroso compounds from a composition that comprises an N-nitroso compound and a desirable product, i.e., usually an organo-amine. The N-nitroso compounds often are formed from the desired compound during manufacture or use, in which case the N-nitroso compound will have a structure very similar to the parent organo-amine. The decomposition of these N-nitroso compounds often leaves as a product the desired parent organo-amine.

The process is applicable whenever 1) the N-nitroso compound begins to decompose at a temperature less than the decomposition temperature of the desired product, and 2) the byproducts of the thermolysis of the N-nitroso compounds do not negate the utility of the desired product, or alternatively the byproducts of the thermolysis of the N-nitroso compounds can be separated from the desired product. This process may be applicable to, but not limited to, certain dinitroaniline herbicides, certain pharmaceuticals, certain pesticides, certain cutting oil formulations, and the like.

The method of this invention comprises heating a composition comprising an N-nitroso compound and a desirable product to a temperature wherein the N-nitroso compound decomposes, but at a temperature less than or near the decomposition temperature of the desirable product, and maintaining the temperature for an effective amount of time.

As used herein, the term "decompose" as it applies to N-nitroso compounds means to change the structure of the molecule such that the N—NO moiety is eliminated by, for example, being broken into a nitric oxide radical and another compound, being substituted thereon, or removed from the compound.

As used herein, the term "temperature less than or near the decomposition temperature of the desired product"means that temperature that may be well above the temperature at which the desired product begins to decompose, but is a temperature such that the entire thermolysis procedure does not decompose too much, i.e., less than 20%, of the desired product. The maximum temperature is therefore a function of the time the composition is exposed to that temperature. Given the constraints of most industrial processes, the maximum temperature will usually be less than about 60 degrees Centigrade above the temperature wherein the desired products in the composition, often the parent organoamines, begin to decompose.

As used herein, the term "decompose"as it applies to the desired parent or product compound means to be altered in any manner which reduces or eliminates the ultimate utility of the desired parent or product compound.

As used herein, the term "an effective amount of time"is that amount of time which, at the temperature profile and reaction conditions chosen, is sufficient for the concentration of N-nitroso compounds to be reduced to the desired level, i.e., to less than 500 ppm, or to less than 1 ppm, or to less than 0.5 ppm.

The method of this invention as it applies to a composition comprising N-nitroso-pendimethalin, also described as N-(1-ethylpropyl)-2,6-dinitro-N-nitroso-3,4-xylidine, and Pendimethalin, also described as N-(1-ethylpropyl)-2,6-dinitro-3,4-xylidine, comprises heating the composition to a temperature wherein the N-nitroso-pendimethalin decomposes, but at a temperature less than or near the decomposition temperature of the Pendimethalin, and maintaining the temperature for an effective amount of time.

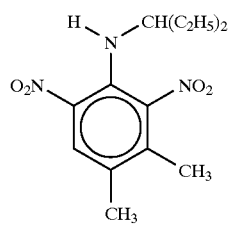

N-(1-ethylpropyl)-2, 6-dinitro-3, 4-xylidine
Pendimethalin

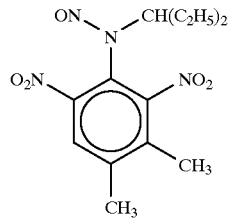

N-(1-ethylpropyl)-2, 6-dinitro-N-nitroso-3, 4-xylidine
N-nitroso-pendimethalin

From the results of accelerating rate calorimetry it was determined that N-nitroso-pendimethalin may begin to thermally decompose at approximately 120° C., whereas the corresponding onset temperature for Pendimethalin itself is approximately 200° C. The rate of decomposition increases exponentially with temperature above the temperature where decomposition begins. The effective time required to reduce the concentration of N-nitroso-pendimethalin in Pendimethalin from a given level to less than 1 ppm will increase linearly with the initial concentration of N-nitroso-pendimethalin but will decrease exponentially with the temperature at which the thermal denitrosation reaction is conducted. Therefore at 120° C. the effective time for satisfactory denitrosation could be on the order of several days whereas the corresponding time at 210° C. could be on the order of minutes. Of course, the reaction would be even faster above 200° C., though at some point the decomposition of Pendimethalin will become significant. The process is both technically and economically valuable provided the decomposition of the desired product is not excessive, and provided the concentration of the N-nitroso compounds decrease, regardless of the highest temperature reached.

Without being bound to a particular theory, the applicants believe the temperature and other conditions are such that the N—NO bond is broken. The energy of the N—NO bond, and therefore the temperature at which thermolysis occurs, depends on the chemical structure of the parent amine. However, the strength of this bond is generally less than the 70–90 kcal per mole typical of C—N, C—C, and C—H bonds. The thermolysis of the N—NO bond and the subsequent formation of the nitrosyl radical —NO or nitric oxide will of course always occur at sufficiently high temperatures (see Krull, I. S. and Wolf, M. H., "Thermal Energy Analysis For N-nitroso Compounds,"American Laboratory, page 84–91, May 1979). However, this process is useful when the temperature selected is that temperature wherein the N-nitroso compounds decompose, but at a temperature wherein the utility of the desired product is not negated.

For some dinitroaniline herbicides the herbicide decomposes or undergoes other reactions at lower temperatures than are required to break the N—NO bond. In the case of Pendimethalin, however, the decomposition temperature of the desired product is, as stated previously, about 200° C., which is significantly higher than the decomposition temperature of N-nitroso-pendimethalin which is about 120° C. This allows for quantitative thermolysis of the N-nitroso-pendimethalin without significant decomposition of Pendimethalin.

Conventional methods of making Pendimethalin, for instance as described in U.S. Pat. No. 4,136,117, produce raw untreated Pendimethalin. Raw untreated Pendimethalin contains between about 10% to about 30% by weight N-nitroso-pendimethalin. It is believed that in the thermolysis of N-nitroso-pendimethalin roughly one half of the N-nitroso-pendimethalin is converted into Pendimethalin, while the remaining half becomes what is believed to be an inert quinone type structure. If the thermolysis is used as the exclusive method of reducing N-nitroso-pendimethalin, a significant quantity of this inert material may result. The prior art processes, such as treatment with hydrochloric acid, have a greater conversion of N-nitroso-pendimethalin to Pendimethalin.

A second disadvantage to treating compositions that contain very high concentrations of N-nitroso compounds is that the instantaneous heat release that accompanies the breaking of the N—NO bond may be difficult to control on a commercial scale.

Therefore, the preferred method of reducing N-nitroso-pendimethalin concentration in crude Pendimethalin is to first treat by a conventional method using a denitrosating chemical to reduce the concentration of N-nitroso-pendimethalin in the Pendimethalin to 2000 ppm or less, preferably 1000 ppm or less, more preferably 500 ppm or less. This process is then followed by the method of the present invention, which will reduce the quantity of N-nitroso-pendimethalin to the desired level. The initial conversion of N-nitroso-pendimethalin to Pendimethalin can be by any conventional method, including but not limited to those methods described in the Background of the Invention, which are incorporated herein by reference. Such methods include, for example, treatment under effective reaction conditions with denitrosating chemicals such as hydrochloric acid or gaseous hydrogen chloride, or with compounds such as $PCl_3$ or $PCl_5$, or with an aqueous solution of hydrogen bromide, sulfamic acid, and some form of sulfite or bisulfite, or with an aqueous solution containing an oxidant such as alkaline persulfate, or with an alkyl acyl halide, or with an acyl halide in combination with an amino-benzoate ester, or with hydrobromo salts of an amino benzoate ester, or with bromine or chlorine, or with ketones or aldehydes in the presence of a strong acid.

The choice of method for the primary conversion of N-nitroso-pendimethalin to Pendimethalin is not important. However, because the primary conversion is not intended to reduce the levels of N-nitroso-pendimethalin to levels near 1 ppm, there is usually no need to employ expensive scavengers and extended reaction times.

Because of cost, treating molten, crude Pendimethalin with gaseous or concentrated hydrochloric acid is preferred. The preferred method is to react the crude Pendimethalin and the hydrochloric acid at sufficient temperature and, if necessary, pressure to convert a substantial fraction, i.e., about 80% or more, of the N-nitroso-pendimethalin originally present to Pendimethalin, with venting to remove NOCl gas. As the concentration of N-nitroso-pendimethalin decreases to about 2000 ppm, this process slows, and below about 1000 ppm or so these prior art methods become very slow without the presence of an excess of NOCl scavengers. It is possible but difficult to reduce the concentration of N-nitroso-pendimethalin to below about 500 ppm without scavengers. Therefore, at the time when the desired intermediate concentration of N-nitroso-pendimethalin is reached, the excess hydrochloric acid is advantageously removed and the treated Pendimethalin is advantageously neutralized and washed, and then the temperature of the Pendimethalin is increased to the selected temperature.

The reaction mass is heated to an appropriate temperature and held there, or alternatively the temperature can be cycled, or can monotonicly increase, or the temperature can be programmed to follow any number of variations. N-nitroso-pendimethalin decomposition can take place at temperatures of about 120° C., but the decomposition rate is unacceptably slow. The decomposition is much faster at 160° C. or higher, wherein the decomposition of N-nitroso-pendimethalin is essentially complete in one day or less. At 170° C. or greater the decomposition of N-nitroso-pendimethalin is essentially complete in eight hours or less, and at 180° C. the decomposition of N-nitroso-pendimethalin is essentially complete within 60 minutes or less. The preferred temperature is therefore about 160° C. or above, more preferably about 170° C. or above, and most preferably about 180° C. or above.

At temperatures near about 200° C. the Pendimethalin itself begins to decompose. The maximum temperature for treating a mixture of N-nitroso-pendimethalin and Pendimethalin with this process is therefore below about 260° C., preferably below about 220° C., more preferably below about 200° C., and most preferably, given the difficulties of controlling temperature, below about 190° C.

The required reaction time necessary to reduce the concentration of N-nitroso-pendimethalin will depend on the temperature profile, the conditions or processes by which nitric oxide is removed from the Pendimethalin, i.e., high or low vacuum, inert gas, scavengers, process conditions which favor removal of nitric oxide from the reaction mass, as well as the initial and final concentrations of N-nitroso-pendimethalin.

Volatile decomposition products are advantageously removed from the molten Pendimethalin. In particular, the byproduct nitric oxide is removed from the Pendimethalin. This prevents the reverse reaction from occurring. Thermolysis is advantageously performed under a vacuum or a stream of inert gas to remove nitric oxide. A hard vacuum, i.e., about 20 millimeters of mercury pressure, is preferred and will result in a lower effective time needed to reduce the N-nitroso compounds to the desired level. A soft vacuum, i.e., about 300 millimeters of mercury pressure, can be employed, but the effective time may be longer. Use on an inert gas, i.e., nitrogen, to sweep nitric oxide from the reaction mixture may be preferred in some instances. Of course, agitating and purging the Pendimethalin with inert gas or vapor such as nitrogen or steam will readily remove nitric oxide. A vacuum is also efficient at removing nitric oxide. Examples of a commercial process to achieve the thermal decomposition of N-nitroso-pendimethalin could include, but not be limited to, the following: batch mode operation with an agitated autoclave reactor or continuous operation of a "wiped" or "falling film" evaporator.

In some cases it may be advantageous to add a nitric oxide scavenger prior to the thermal denitrosation step. Typical nitric oxide scavengers include urea, sulfamic acid, ammonium chloride, and the like.

Under certain treatment conditions described herein, Pendimethalin so treated contains less than 1 ppm N-nitroso-pendimethalin. The reduction of nitrosamines appear to be final and irreversible.

EXAMPLES

The following examples are included to demonstrate embodiments of the invention. However, those of skill in the art should, in light of the present disclosure, appreciate that many changes can be made in the specific embodiments which are disclosed and still obtain a like or similar result without departing from the spirit and scope of the invention.

Example 1

A sample of crude Pendimethalin containing 15 weight percent of N-nitroso-pendimethalin was made according to the procedure described in U.S. Pat. No. 4,521,157. Primary denitrosation was achieved by treating the sample with HCl and urea according to the procedure of U.S. Pat. No. 4,136,117. After 10 hours of treatment at 82° C., the concentration of N-nitroso-pendimethalin had decreased to 228 ppm. This material was then neutralized and recovered as a solid after evaporation of the chlorinated hydrocarbon solvent. A 120 mg sample of this solid was heated to its melting point (~50° C.), treated with 3 mg of urea and then heated to 180° C. under a stream of nitrogen gas for 15 minutes. The recovery of Pendimethalin was essentially quantitative and the concentration of N-nitroso-pendimethalin had decreased to 0.6 ppm.

Example 2

A sample of crude Pendimethalin containing 18 weight percent of N-nitroso-pendimethalin was synthesized according to the procedure described in U.S. Pat. No. 4,621,157. Primary denitrosation was achieved by treating the crude, molten sample with a 5 molar excess of 37% HCl (based on contained N-nitroso-pendimethalin) at 105° C. After 1.5 hours, the concentration of N-nitroso-pendimethalin had decreased to <1.0 weight percent. The molten product was neutralized with dilute caustic and washed with hot water and cooled to room temperature. A 120 mg sample of the resulting solid was heated to 170° C. under 20 mm Hg vacuum for 15 minutes. The recovery of Pendimethalin was essentially quantitative and the concentration of N-nitroso-pendimethalin had decreased to 0.8 ppm.

Example 3

A 120 mg sample of the same crude Pendimethalin obtained from the primary HCl denitrosation described in Example 2 was heated to 170° C. under a stream of nitrogen gas for 15 minutes. The recovery of Pendimethalin was essentially quantitative and the concentration of N-nitroso-pendimethalin had decreased to 12 ppm.

What is claimed is:

1. A method of reducing the concentration of an N-nitroso-containing compound in a composition comprising a desired dinitroaniline herbicide and the N-nitroso derivative of the dinitroaniline herbicide, the method comprising heating the composition to a temperature wherein the N-nitroso derivative of the dinitroaniline herbicide decomposes, but at a temperature less than or near the decomposition temperature of the desired dinitroaniline herbicide, and maintaining the temperature for an effective amount of time.

2. The method of claim 1 wherein the temperature is from about 100° C. to about 260° C.

3. A method of reducing the concentration of N-nitroso-pendimethalin in a composition comprising N-nitroso-pendimethalin and Pendimethalin, the method comprising heating the composition to a temperature wherein the N-nitroso-pendimethalin decomposes, but at a temperature less than or near the decomposition temperature of the Pendimethalin, and maintaining the temperature for an effective amount of time.

4. The method of claim 3 wherein the decomposition of the N-nitroso-pendimethalin produces nitric oxide, and wherein the nitric oxide is removed from the composition by one or more of venting, vacuum, purging with an inert gas, and reaction with an nitric oxide scavenger.

5. The method of claim 3 wherein the temperature is from about 120° C. to about 260° C.

6. The method of claim 3 wherein the temperature is from about 160° C. to about 220° C.

7. The method of claim 3 wherein the temperature is from about 170° C. to about 200° C.

8. The method of claim 3 wherein the temperature is from about 180° C. to about 190° C.

9. A method of reducing the concentration of N-nitroso-pendimethalin in a composition comprising Pendimethalin and N-nitroso-pendimethalin, said method comprising reacting the composition with a denitrosating chemical under conditions that reduce the concentration of N-nitroso-pendimethalin, and then heating the denirosated composition to a temperature wherein the N-nitroso-pendimethalin decomposes, but at a temperature less than or near the decomposition temperature of the Pendimethalin, and maintaining the temperature for an effective amount of time.

10. The method of claim 9 wherein said method additionally comprises removing the denitrosating chemical prior to heating the composition.

11. The method of claim 9 wherein said method additionally comprises removing nitric oxide from the composition for at least a portion of the time the composition is being heated.

12. The method of claim 9 wherein the denitrosating chemical is hydrochloric acid gas or aqueous hydrochloric acid.

13. The method of claim 9 wherein the concentration of N-nitroso-pendimethalin in the denitrosated composition after reacting the composition is 2000 ppm by weight or less.

14. The method of claim 9 wherein the concentration of N-nitroso-pendimethalin in the denitrosated composition after reacting the composition is 1000 ppm by weight or less.

15. The method of claim 9 wherein the concentration of N-nitroso-pendimethalin in the denitrosated composition after reacting the composition is 500 ppm by weight or less.

16. The method of claim 9 wherein the temperature is from about 120° C. to about 260° C.

17. The method of claim 9 wherein the temperature is from about 160° C. to about 220° C.

18. The method of claim 9 wherein the temperature is from about 170° C. to about 200° C.

19. The method of claim 9 wherein the temperature is from about 180° C. to about 190° C.

20. The method of claim 19 wherein the removal of nitric oxide from the composition is accomplished by maintaining a partial vacuum.

21. The method of claim 19 wherein the removal of nitric oxide from the composition is accomplished by purging the composition with an inert gas.

22. The method of claim 19 wherein the removal of nitric oxide from the composition is accelerated by the addition of a nitric oxide scavenger.

23. The method of claim 18 wherein the effective period of time is from about 5 minutes to about 8 hours.

24. The method of claim 19 wherein the effective period of time is from about 5 minutes to about 60 minutes.

* * * * *